United States Patent [19]
Roelant

[11] Patent Number: 6,001,573
[45] Date of Patent: *Dec. 14, 1999

[54] USE OF PORPHYRINS AS A UNIVERSAL LABEL

[75] Inventor: Chris Roelant, Leuven, Belgium

[73] Assignee: Packard Bioscience B.V., Gronigen, Netherlands

[ * ] Notice: This patent is subject to a terminal disclaimer.

[21] Appl. No.: 08/956,856

[22] Filed: Oct. 23, 1997

Related U.S. Application Data

[63] Continuation-in-part of application No. 08/876,093, Jun. 13, 1997.

[30] Foreign Application Priority Data

Jun. 14, 1996 [EP] European Pat. Off. .............. 96201674
Oct. 31, 1996 [US] U.S. ..................... 60029528

[51] Int. Cl.$^6$ ................................................ C12Q 1/68
[52] U.S. Cl. .............................................. 435/6; 530/350
[58] Field of Search .................. 455/6; 530/350

[56] References Cited

U.S. PATENT DOCUMENTS

| | | | |
|---|---|---|---|
| 3,754,868 | 8/1973 | Witz et al. ............................ | 23/254 R |
| 4,176,007 | 11/1979 | Jeffers et al. ............................. | 435/34 |
| 4,234,681 | 11/1980 | DeLuca-McElroy ....................... | 435/8 |
| 4,375,972 | 3/1983 | Forgione et al. ......................... | 436/531 |
| 4,485,086 | 11/1984 | Wong ....................................... | 424/1.1 |
| 4,577,636 | 3/1986 | Spears ..................................... | 128/654 |
| 4,614,723 | 9/1986 | Schmidt et al. ......................... | 436/536 |
| 4,659,676 | 4/1987 | Rhyne, Jr. ............................... | 436/56 |
| 4,672,039 | 6/1987 | Lundblom ............................... | 435/291 |
| 4,803,170 | 2/1989 | Stanton et al. .......................... | 436/518 |
| 4,933,276 | 6/1990 | Baret ....................................... | 435/7 |
| 4,994,737 | 2/1991 | Stavrianopoulos ......................... | 435/6 |
| 5,108,893 | 4/1992 | Baret ....................................... | 435/6 |
| 5,242,842 | 9/1993 | Sundrehagen ............................ | 436/536 |
| 5,306,624 | 4/1994 | Roelant ..................................... | 435/39 |
| 5,328,824 | 7/1994 | Ward et al. ................................ | 435/6 |
| 5,340,714 | 8/1994 | Katsilometes ............................ | 435/6 |
| 5,494,793 | 2/1996 | Schindele et al. .......................... | 435/6 |
| 5,627,028 | 5/1997 | Tai et al. ..................................... | 435/6 |

FOREIGN PATENT DOCUMENTS

| | | |
|---|---|---|
| 0070685 | 1/1983 | European Pat. Off. . |
| 0480361 | 4/1992 | European Pat. Off. . |
| 62-135769 | 6/1987 | Japan . |
| 3-47093 | 2/1991 | Japan . |
| 2063469 | 6/1981 | United Kingdom . |
| WO93/12809 | 7/1993 | WIPO . |

OTHER PUBLICATIONS

European Search Report, dated Mar. 17, 1997, from The Hague, by Examiner A. Wells, issued for Application No. EP 96 20 1674.

Adam, Yves et al, "Luminol and Isoluminol Chemiluminescence Reaction Catalyzed by Synthetic Water–Soluble Metalloporphyrins", *New Journal of Chemistry*, vol. 16, No. 4, pp. 525–528, Apr. 1992.

Ewetz, L. et al. "Factors Affecting the Specificity of the Luminol Reaction with Hematin Compounds", *Analytical Biochemistry*, vol. 71, No. 2, pp. 564–570, Apr. 1976.

Olsson, T. et al, "Catalytic Action and Destruction of Protohematin During Peroxide Dependent Luminol Chemiluminescence", *Photochemistry and Photobiology*, vol. 38, No. 2, pp.223–229, Aug. 1983.

*Primary Examiner*—Scott W. Houtteman
*Attorney, Agent, or Firm*—Arnold White & Durkee

[57] ABSTRACT

A process is provided for using porphyrin or porphyrin derived compounds as universal labels for various assays and other quantification techniques without the need for a bridging agent to couple the label to the target particles. Particles which can be labeled include beads, microorganisms, cells, and molecules. The porphyrin label irreversibly attaches to target particles and afterwards can be detected and quantified by any number of ways, such as chemiluminometrically, fluorometrically or radiometrically in an amount which is proportional to the number of labeled particles.

33 Claims, 8 Drawing Sheets

USE OF PORPHYRINS AS A UNIVERSAL LABEL

This is a continuation in part of application Ser. No. 08/876,093, filed Jun. 13, 1997.

TECHNICAL FIELD OF THE INVENTION

The present invention relates to a process for the labeling, detecting, and quantifying of particles (e.g., molecules, beads, microorganisms and cells).

BACKGROUND OF THE INVENTION

Typically, particles including molecules, beads, microorganisms and cells are detected and quantified directly by microscopic, nephelometric or electronic enumeration, or indirectly, by the measurement of microorganism or cell metabolic activity, the use of chromogenic or fluorogenic dyes, or the incorporation of radioactive precursors (e.g., a compound containing a radioactive metal isotope). When employed for detection and quantification, the chromogenic or fluorogenic dyes and the radioactive precursors are attached to the particles to be detected and quantified. As such, the chromogenic or fluorogenic dyes and the radioactive precursors act as labels for the detection of the target particle.

However, labeling of particles by means of chromogenic or fluorogenic dyes and radioactive precursors often requires intermediate bridging molecules or functional groups, or metabolic processing to couple the target particle to the label. These methods, employing a bridging agent, are labor intensive and often require long incubation and processing times.

The use of porphyrin (or porphin) and its many derivatives as labels for various assays is known in the art. Porphyrins are tetrapyrrolic pigment macrocycles which may be found free in nature but which more commonly occur as complexes with metal ions, typically divalent metal ions. The base porphyrin structure is indicated in Formula 1. The numbers (1–8) indicate the positions at which groups can be attached to form the different porphyrin derivatives.

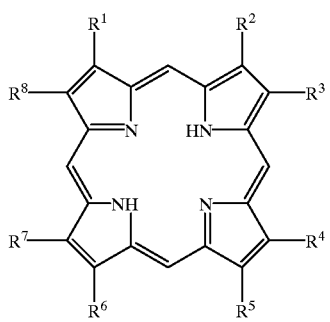

In various derivatives, individual groups may be present at each of the numbered substitution points. Examples of such derivatives include aetioporphyrin which exists as four different isomers in which the beta hydrogens of each pyrrole group have been replaced with a methyl and an ethyl group. Uroporphyrin is similar except that acetic acid and propionic acid groups are used instead of methyl and ethyl groups. Coproporphyrins similarly contain four methyl and four propionic acid groups. A final exemplary group are the protoporphyrins, a group of fifteen isomers having four methyl groups, two vinyl groups, and two propionic acid groups at positions 1–8. Shown below as Formula 2 is protoporphyrin IX.

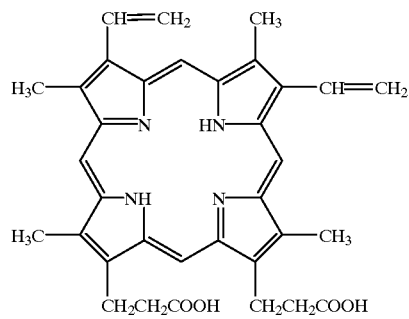

In other derivatives, a single substitution may cause both of the numbered positions of each pyrrole group to be occupied. Phthalocyanine is typical of the porphyrin derivatives of this type. Phthalocyanine is also characterized by the presence of four nitrogen atoms which provide the link between the four pyrrole groups of the porphyrin nucleus. In the original porphyrin and the derivatives previously described, this linkage was provided by carbon atoms having a single terminal hydrogen atom bonded to each carbon. Shown below as Formula 3 is phthalocyanine.

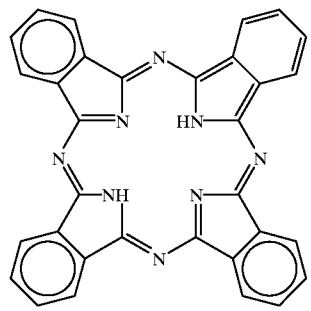

As previously indicated, porphyrin and its various derivatives are typically complexed with metals. When this occurs, the two hydrogen atoms bonded to the nitrogen atoms of two diagonally opposed pyrrole groups are replaced by a single metal atom, M, as indicated in Formula 4.

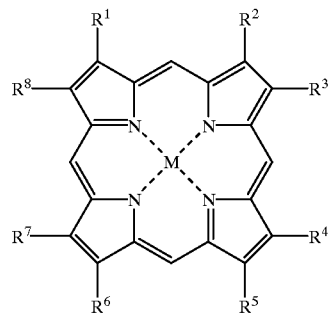

Typical metals, M, which can be incorporated into the porphyrin structure are Iron (Fe), Cobalt (Co), Gallium (Ga), Tin (Sn), Zinc (Zn), Chromium (Cr), Magnesium (Mg), and the various elements of the lanthanide series. The various derivatives of the base porphyrin can be similarly complexed with a metal (M).

Porphyrin and its derivatives (hereafter referred to as porphyrin) have been successfully employed as labels (or markers) in immunoassays, nucleic acid probe assays, immunoblotting, hybridization assays, microscopy, imaging, flow cytometry, DNA sequencing, and photodynamic therapy. However, the use of porphyrin and its derivatives as a label for the chemiluminometric, radiometric, or fluorometric detection of a particle in these various assays and techniques has heretofore required that a bridging agent be used. In the art, the use of a bridging agent may be indicated by various terms, including but not limited to bridged(ing), coupled(ing), conjugated, linkage, and tethered. The bridging agent whether it is a molecule reactant or functional group couples the porphyrin label to the particle to be detected and quantified. The choice of porphyrin and bridging agent will vary significantly depending upon numerous criteria including the nature of the target particle, the media in which the target particle is located, and the means of detection to be employed. The bridging agent providing the linkage can be substituted onto the porphyrin at any number of possible positions, including for example one of the beta positions of a pyrrole group, a terminal position on some group substituted at the pyrrole group (e.g., replacing a hydrogen bound to a carbon of the six-member ring characteristic of phthalocyanine), or a terminal position at the carbon linking the pyrrole groups. The bridging agent may be substituted on the porphyrin at a single position or optionally it may be substituted at multiple positions. Positions at which the bridging device has been substituted onto the porphyrin but at which coupling does not occur may provide increased solubility. Indeed, substituents may be provided on to the porphyrin for the sole purpose of increasing solubility.

Numerous bridging agents (i.e., functional groups) are known in the art. They include but are not limited to sulfonic acid groups (—$SO_3H$), sulfonate groups (—$SO_3^-$, $X^+$), carboxylic acid groups (—$CO_2H$), carboxylate groups (—$CO_2^{2-}$, $X^+$), phosphoric acid groups (—$PO_4H_2$), phosphate groups (—$PO_4^-$, $2X^+$), phosphonate groups (—$PO_3^-$, $X^+$ or —$PO_3H$), hydroxy or phenoxy groups (—OH), amino groups (—$NH_2$) and ammonium and pyridinium groups (—$NR_4^+$, $X^-$). Additionally, one of the most common ways to provide linkage is to form a water soluble carbodiimide derivative of the porphyrin. Optionally, the bridging agent can be coupled to the target particle first prior to its exposure to the porphyrin label.

In other detection methods, such as nucleic acid probe assays, it may be necessary to bind the porphyrin label to a nucleic acid primer or probe. A bridging agent, which may be initially bound to either the porphyrin label, the primer or probe, or the target particle, is used to effect the coupling of the porphyrin to the primer or probe. The primer or probe subsequently attaches itself to the target particle. There is a need for a detection process utilizing porphyrin labels that does not require a bridging agent for the binding of the porphyrin label to the target particle.

SUMMARY OF THE INVENTION

The present invention provides a universal label, which by itself and without bridging agents irreversibly attaches to target particles, including molecules, beads, microorganisms and cells and afterwards can be detected either chemiluminometrically, fluorometrically or radiometrically in an amount which is proportional to the number of labeled particles.

The quest for an universal label is satisfied by the use of porphyrins in chemiluminescent, fluorescent or radioactive compositions. In particular, the present invention relates to chemiluminescent, fluorescent, or radioactive compositions which comprise a porphyrin of the following Formula 5 (which depicts the same structure as Formula 4):

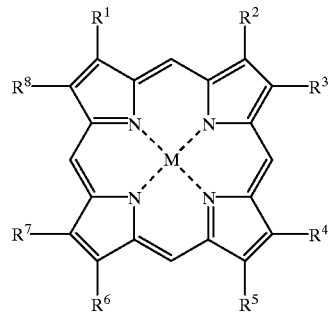

wherein $R^1$–$R^8$ can be —$CH_3$, —$CH_2$—$CH_3$, —$CH_2$=$CH_2$, —$COCH_3$, —CHO, —$CH_2$—$CH_2OH$, —CH=CHOOH, or phenyl and M can be Iron (Fe), Cobalt (Co), Gallium (Ga), Tin (Sn), Zinc (Zn), Chromium (Cr), Magnesium (Mg), and the various elements of the lanthanide series.

In accordance with one aspect, the present invention contemplates a process of labeling, detecting and quantifying particles, said particles including without limitation molecules, beads, microorganisms or cells, which process comprises the steps of:

a) mixing porphyrin, in the absence of a bridging agent, with said particles for a time sufficient for the porphyrin to bind to the particles;

b) separating the porphyrin labeled particles from the unbound porphyrin; and c) quantifying said porphyrin labeled particles.

For the different detection and quantification methods, the basic process framework will vary in accordance with the general procedures of the technique. For chemiluminometric methods, the porphyrin labeled particles are exposed to a stabilized mixture of a luminescent probe and oxidizer (or oxidant) which produces luminescence upon destabilization of the porphyrin attached to the particles. The emission of light from the stabilized mixture of luminescent probe and oxidizer is detected. The quantity of light emitted is proportional to the number porphyrin labeled particles.

For radiometric methods, radiation emission of isotope-labeled porphyrins attached to the particles is detected. The quantity of radiation emitted is proportional to the number of porphyrin labeled particles.

For fluorometric methods, fluorescence emitted after light excitation of porphyrin labeled particles is detected. The quantity of light emitted is proportional to the number of porphyrin labeled particles.

In accordance with another aspect, the present invention contemplates adhesion or binding assays comprising the steps of:

a) providing a suspension of particles to be tested;

b) mixing porphyrin, in the absence of a bridging agent, with said suspension;

c) separating porphyrin labeled particles from unbound particles by methods such as centrifugation, magnetic separation, or filtration;

d) incubating the porphyrin labeled particles with a target surface;

e) removing non-adherent or non-bound labeled particles; and f) quantifying the surface adherent or bound labeled particles by methods such as radiometric, fluorometric, or chemiluminometric processes.

In accordance with yet another aspect, the present invention provides a particle diameter or surface size analysis process comprising the steps of:
a) providing a suspension of a predetermined number of particles to be tested;
b) mixing porphyrin, in the absence of a bridging agent, with the suspension;
c) removing excess porphyrin by a method such as centrifugation, magnetic separation, or filtration;
d) obtaining a radiometric, fluorometric, or chemiluminometric signal generated by the predetermined number of particles; and
e) calculating the signal per particle as an indication of the diameter or surface size of the particles.

In accordance with yet another aspect, the present invention provides in vitro or in vivo uptake studies comprising the steps of:
a) providing a suspension of particles to be studied;
b) mixing porphyrin, in the absence of a bridging agent, with the suspension;
c) removing excess porphyrin by a method such as centrifugation, magnetic separation, and filtration;
d) resuspending labeled particles in an appropriate medium;
e) injecting the labeled particles and appropriate medium into biologic objects; and
f) tracing the injected particles.

In accordance with yet another aspect, the present invention provides assay kits for quantifying particles, beads, microorganisms or cells. The elements contained within the assay kit will vary depending upon the detection and quantification method to be employed: chemiluminometric, radiometric, or fluorometric. In all cases the assay kit will consist of a first container containing at least a porphyrin label. For chemiluminometric detection, the assay kit contains a first container containing a porphyrin label and a second container containing a stabilized mixture of luminescent probe and oxidizer. For radiometric detection, the assay kit contains a first container containing an isotopically labeled porphyrin and a second container containing either, a scintillation cocktail or SPA (scintillation proximity assay beads). For fluorometric detection, the assay kit contains a container containing porphyrin label.

DETAILED DESCRIPTION OF THE INVENTION

Figure 1:
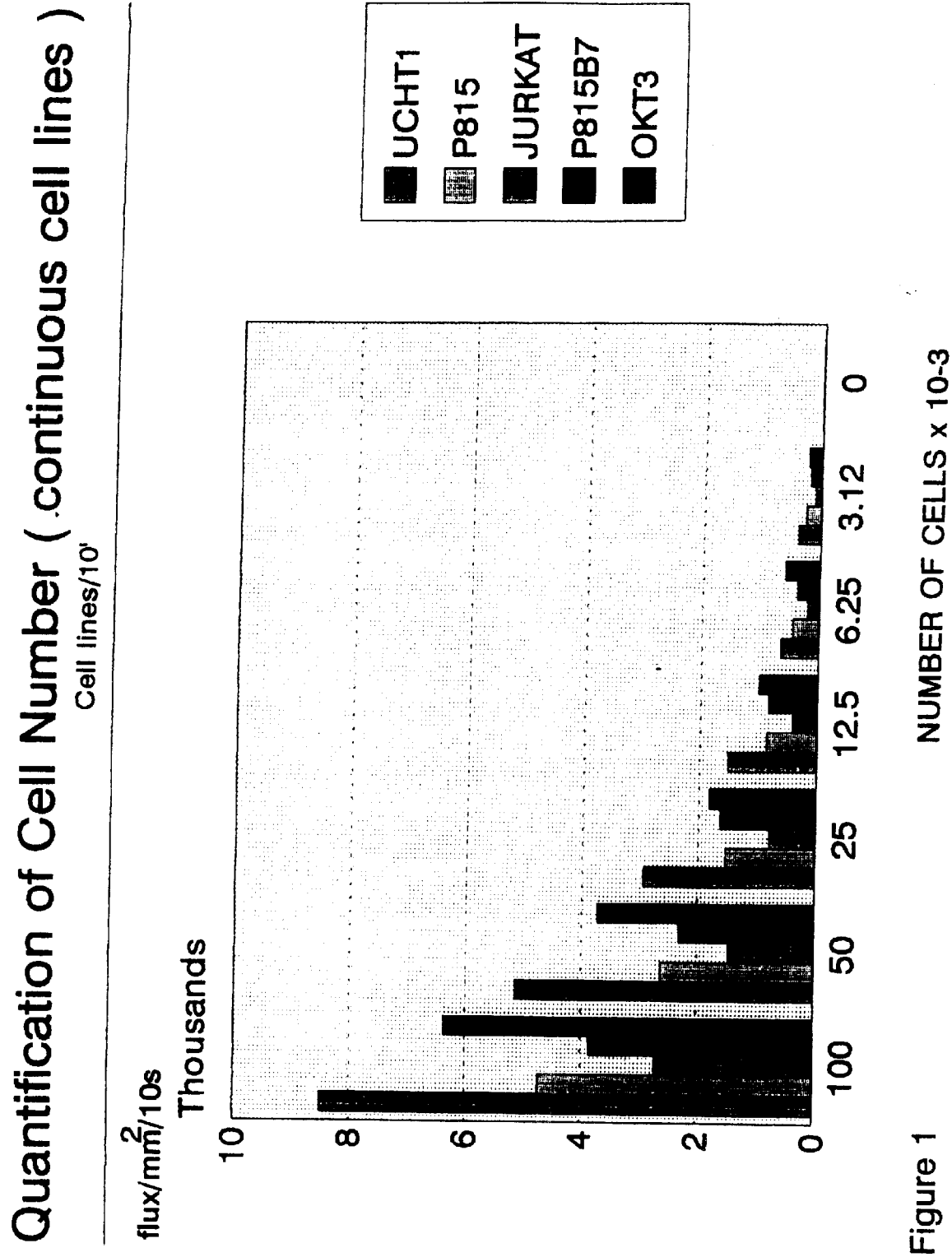
FIGS. 1 and 2 show labeling used in quantifying cell number.

In one embodiment, a process is provided for detecting or quantifying the number of porphyrin labeled particles, including molecules, beads, microorganisms or cells, bound to target surfaces. In accordance with this embodiment, an effective detection amount of ferriprotoporphyrin is mixed with an aqueous suspensions of target particles. After removal of excess porphyrin label, either by centrifugation, magnetic separation or filtration, labeled particles are suspended at required densities in aqueous solutions of choice.

The labeled particles are then added to target surfaces, maintained under required reaction conditions for a period of time sufficient to bind or to adhere. After this time, which will vary as known to those of ordinary skill in the art with the conditions employed, non-bound or non-adherent labeled particles are removed. Adherent or bound labeled particles are detected and quantified by desired detection methods, including chemiluminometric, radiometric, and fluorometric methods.

For chemiluminometric methods, the desired aqueous solution of choice contains a sufficient amount of a stabilized mixture of luminescent probe (precursor) and oxidizer. Any resultant chemiluminescence is detected and quantified. The chemiluminescence is proportional to the number of porphyrin labeled adherent or bound particles.

Chemiluminescence precursors for use in the present invention include 2,3-dihydro-1,4-phthalazinediones characterized by generally by Formula 6.

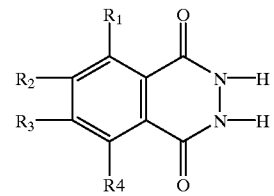

In Formula 6, $R_1$ is an amino group, and each of the $R_2$, $R_3$ and $R_4$ groups is optionally substituted. Particularly preferred as a chemiluminescence precursor is 5-amino-2,3-dihydro-1,4-phthalazinedione (luminol).

In one variation for carrying out the present embodiment in conjunction with chemiluminometric detection methods, porphyrin labeled adherent or bound particles positioned on a solid surface (i.e. membranes, dipsticks) and enclosed in a transparent container or microplate with a transparent well bottom are placed on a high speed photographic film, such as a Polaroid film cartridge. Immobilized labeled particles are detected following the injection of a stabilized mixture of luminescent probe and oxidizer into the vessel. The stabilized mixture contacts the adherent or bound particles emitting light by virtue of a reaction between the mixture of luminescent probe, oxidizer and porphyrin labeled particles. The emitted light is subsequently detected on the film. Alternatively, the emitted light can be detected by other means known in the art, such as by a photomultiplier tube (PMT) or charge coupled device (CCD) cameras.

When chemiluminometric detection is desired, any oxidant which reacts with the porphyrin to cause excitation of the chemiluminescence precursor so that it emits light in a luminescence reaction, may be employed in the present invention. Particularly preferred oxidants are peroxides, e.g., hydrogen peroxide, and perborate ions or the like generated in situ by enzymatic reactions.

It may additionally be desirous to employ buffering substances in the chemiluminometric method. Suitable buffering substances that can be employed are phosphate, tris (hydroxymethyl) aminomethane, carbonate and borate. Additional stabilization of mixtures of luminescent precursor and oxidizer may be obtained by the addition of chelators such as deferrioxamine or ethylenediaminetetraacetic acid (EDTA).

The following reagent composition of luminescent precursor, stabilizer and oxidizer is particularly suitable for use in embodiments where chemiluminometric detection methods are employed: 0.1 M borate buffer, pH 9.50, containing 6.5 mM perborate, 3.4 mM EDTA, and 0.1 mM luminol.

An effective detection amount of porphyrin is that amount of porphyrin needed to provide a detectable luminescent signal in proportion to the number of particles to be counted. An effective detection amount varies inter alia with the number and nature of the particles and the nature of the porphyrin.

Where the number of particles, beads, microorganisms or cells is from about 0 to about $10^9$/milliliter (ml) and the luminescent probe is luminol, an effective detection amount of porphyrin, used for labeling, is from about $10^{-3}$ M to about $10^{-5}$ M.

Labeling and detection conditions include: temperature, pH value, osmolality, tonicity and the like. Typically, temperature can range from about 5° C. to about 50° C. and, preferably from about 20° C. to about 40° C. The pH for labeling can range from about 6 to about 8.5 and, preferably from about 6.5 to about 7.5. Detection pH can range from about 7.5 up to about 12.5 and preferably from a value of about 8 to a value of about 10.5. Maintenance time of porphyrin labeling is between about 5 and up to about 20 minutes, preferably about 10 minutes.

For radiometric methods, radiation emission of isotopically labeled porphyrins attached to the particles is detected and quantified. The quantity of emitted radiation is proportional to the number of porphyrin labeled particles. The desired aqueous solution of choice contains a sufficient amount of an appropriate scintillation cocktail. The target particles is bound to an isotope (beta emitter marker) containing porphyrin label. Emitted radiation is detected by PMT or CCD cameras. Alternatively, emitted radiation of particles labeled with an isotope marked porphyrin and adhering to or bound to surfaces coated with an appropriate solid scintillator can be detected directly by PMT.

Suitable beta-emtting isotopes that can be used with radiometric techniques include carbon-14, chlorine-36, cobalt-(57, 58, 60), gadolinium-153, iron-(55, 59), nickel-63 tritium, For fluorometric methods, the adherent labeled particles are exposed to a beam of light of which the wavelength matches the excitation wavelength of the porphyrin label. After or during the excitation of the porphyrin label, the emission of light by the excited porphyrin is detected by a CCD camera or by PMT. The quantity of light emitted is proportional to the number of porphyrin labeled particles.

Non-limiting examples of beads which can be utilized as target particles with the embodiments of the present invention include particles or beads made of nylon, plastic, polystyrene, polypropylene, latex, glass. A bead means either a solid sphere or hollow sphere, including liposomes and size ranging from submicroscopic to about 1 cm. In addition these particles or beads may carry ligands, haptens or bridge molecules such as biotin, biotin-N-hydroxysuccinimide or binding proteins including antibodies, avidin and streptavidin. Non-limiting examples of microorganisms which can be utilized as target particles with the embodiments of the present invention include gram negative and gram positive bacteria, mycoplasma, viruses. Non-limiting examples of cells which can be utilized as target particles with the embodiments of the present invention include prokaryotic as well as eukaryotic and mammalian cell types. As used herein, a particle can also mean any particulate phase with undefined shape, including molecules, micelles, and coloids with the size of the particle ranging from submicroscopic to about 1 cm.

It should be evident that the applicability of the described process is extremely broad. Any particle for which porphyrin has previously been used as a label can utilized with the described process. See, for example, U.S. Pat. No. 5,494, 793. As an indication of this the following is a non-limiting list of particles that can be detected: drugs, drug metabolites, hormones, peptides, nucleotides, neurotransmitters, cholesterol, growth factors, oligonucleotides, antibodies, antigen-binding fragments, serum proteins, enzymes, polynucleotides, intracellular organelles, cell surface antigens, avidin, biotin, binding proteins, nucleic acids, membrane probes, and nucleic acid probes.

The process can utilized for any of the numerous purposes and detection techniques previously employing labels. See, for example, U.S. Pat. Nos. 5,494,793; 5,340,714; 5,306, 624; 4,994,373; 4,659,676; 4,614,723; and 4,485,086. Techniques which can be employed wit the process include, but are not limited to, competitive, displacement, or sandwich immunoassays; nucleic acid probe assays; immunoblotting; hybridization assays; microscopy; imaging; flow cytometry; DNA sequencing; and photodynamic therapy.

Non-limiting examples of porphyrins which can be utilized with the embodiments of the present invention include metal-complexed protoporphyrins. Preferred metal protoporphyrins are ferri-protoporphyrins, particularly ferroprotoporphyrin IX and those porphyrin deducted from it. This porphyrin-derived structure, depicted in Formula 7, is the prosthetic group of hemoglobin, myoglobin, erythrocruorin, catalase, peroxidase and cytochromes of Class B.

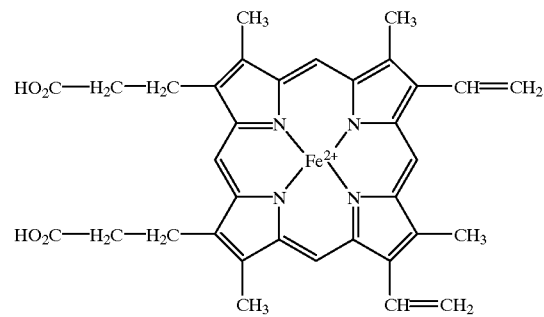

In particular, ferroprotoporphyrins, e.g., chlorohemin (Formula 8) or hematin (Formula 9) are examples which very efficiently add to target particles and which very efficiently fluoresce or trigger the chemiluminescence as described.

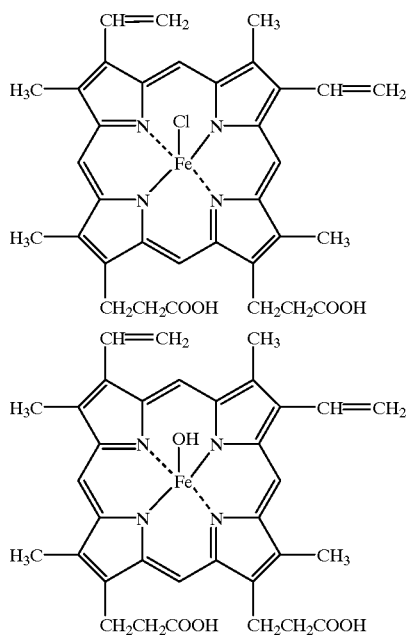

In another embodiment, a process for detecting and quantifying SPA (scintillation proximity assay) beads, adherent or in suspension is provided which comprises the steps of:
a) mixing an isotope labeled porphyrin with an aqueous suspension in which SPA beads needing to be detected and quantified are present; and
b) measuring any increase in radiation emission.

The increase in emitted radiation in this instance is proportional to the number of beads present in the suspension.

In yet another embodiment, an assay kit for detecting and quantifying particles, including beads, microorganisms, cells, and molecules is provided. The assay kit contents will vary depending upon the detection method to be employed, but will generally contain a first container containing a porphyrin label. If radiometric detection is desired, the porphyrin should be radioactively labeled with a suitable beta emitting isotope. The porphyrin label can be suspended or dissolved in a suitable medium or can be in a dry form. The only limitation on the formulation is that a particular formulation provide stability to the label such that the label does not undergo chemical alteration during storage.

The assay kit can further compromise a second container with contents that will vary depending upon the detection method to be employed. If chemiluminometric detection is desired, the second container will contain a stabilized mixture of luminescence precursor and oxidizer, in an amount sufficient to perform at least one quantification assay. The stabilized mixture interacts with particles, including beads, microorganisms, molecules and cells, labeled with the porphyrin label of the first container in an amount proportional to their number. The stabilized mixture of luminescence precursor and oxidizer can also exist as a suspension, solution, or in dry form (e.g., tablets). Suitable buffers or chelators may also be present.

For radiometric detection, the second container will contain a suitable scintillation cocktail for the detection of porphyrin isotopically labeled with a beta-emitter. The scintillation cocktail will be present in an amount sufficient to perform at least one quantification assay.

By way of example, an exemplary kit suitable for chemiluminometric detection comprises a first container containing 1 ml of 1.5 mM hematin (porphyrin label) in dimethylsulfoxide (DMSO) and a second container containing 110 ml of 6.5 mM sodiumperborate (oxidizer), 3.5 mM EDTA as a stabilizer, and 0.1 mM luminol (luminescence precursor) in a 0.1 M borate buffer of pH 9.5. If stored properly at about 4° C., those solutions remain stable for several months.

In a preferred embodiment, the first and second container are labeled with indicia setting forth the nature, amount or concentration and effective amounts of the ingredients contained herein.

In other embodiments, the chemiluminometric, radiometric, and fluorometric techniques described can be used to measure the particle diameter or surface size of target particles. This is accomplished by using a known quantity of particles with one of the previously described techniques. The amount of signal detected per particle is an indication of the diameter or size of the particle.

In other embodiments, the chemiluminometric, radiometric, and fluorometric techniques described can be used for in vitro and in vivo uptake studies. For these purposes, the porphyrin labeled particles, once separated from excess porphyrin, are resuspended in an appropriate medium and injected into the target biological objects. The labeled particles can then be traced by chemiluminometric, radiometric, and fluorometric techniques.

The following examples illustrate particular embodiments of the present invention and are not limiting of the claims or specification in any way.

EXAMPLE 1

Quantification of Cell Number (Continuous Cell Lines)

Materials and Methods

UCHT1, P815, Jurkat T-cells, P815B7 and OKT3 cells were collected, centrifuged and resuspended in Dulbecco's PBS at a density of $1.10^6$ cells/ml in a standard 15 ml Falcon tube.

Next, 10 µl of a hematin stock solution (1 mg/ml in DMSO) was added to 1 ml of each cell suspension and left after gentle mixing at room temperature for about 10 minutes.

After another gentle mixing, cells were left for another 5 minutes at room temperature. Afterwards, 4 ml of PBS were added, and the cells were gently aspirated. After centrifugation at 150 g, 10 minutes, cell pellets were resuspended in another 4 ml of PBS and washed again to make sure all excess hematin label was removed.

Finally, cell pellets were resuspended at a density of $10^6$/ml. Next, cells were plated into individual wells of a white microtiter plate so that the number of cells ranged from about 0 cells/well to about 100,000 cells/well in a total volume of about 100 µl PBS/well.

Detection of the Chemiluminescence

Next, 100 µl of a stabilized luminol/perborate composition (0.1 M borate buffer pH 9.5 containing 6.5 mM perborate, 3.4 mM EDTA and 0.1 mM luminol were added to each well. The chemiluminescence (in flux/mm$^2$/10 s) produced after 10 minutes was recorded at ambient temperature using a charged coupling device (CCD) camera. Results are shown in the attached FIG. 1.

EXAMPLE 2

Quantification of Cell Number (Isolated Cells)

Macrophages, isolated by bronchial lavage of mice, were pooled and concentrated after washing in Dulbecco's PBS at a density of $10^5$/ml. Next, 10 μl of hematin (1 mg/ml in DMSO) were added to a 1 ml macrophage suspension. The cells were incubated and washed as set forth above in Example 1.

Emitted chemiluminescence (flux/mm$^2$/10 s) was detected, 10 minutes after exposure of cells to 100 μl of stabilized luminol/oxidizer composition as set forth above in Example 1. Results are shown in the attached FIG. 2.

Figure 2:
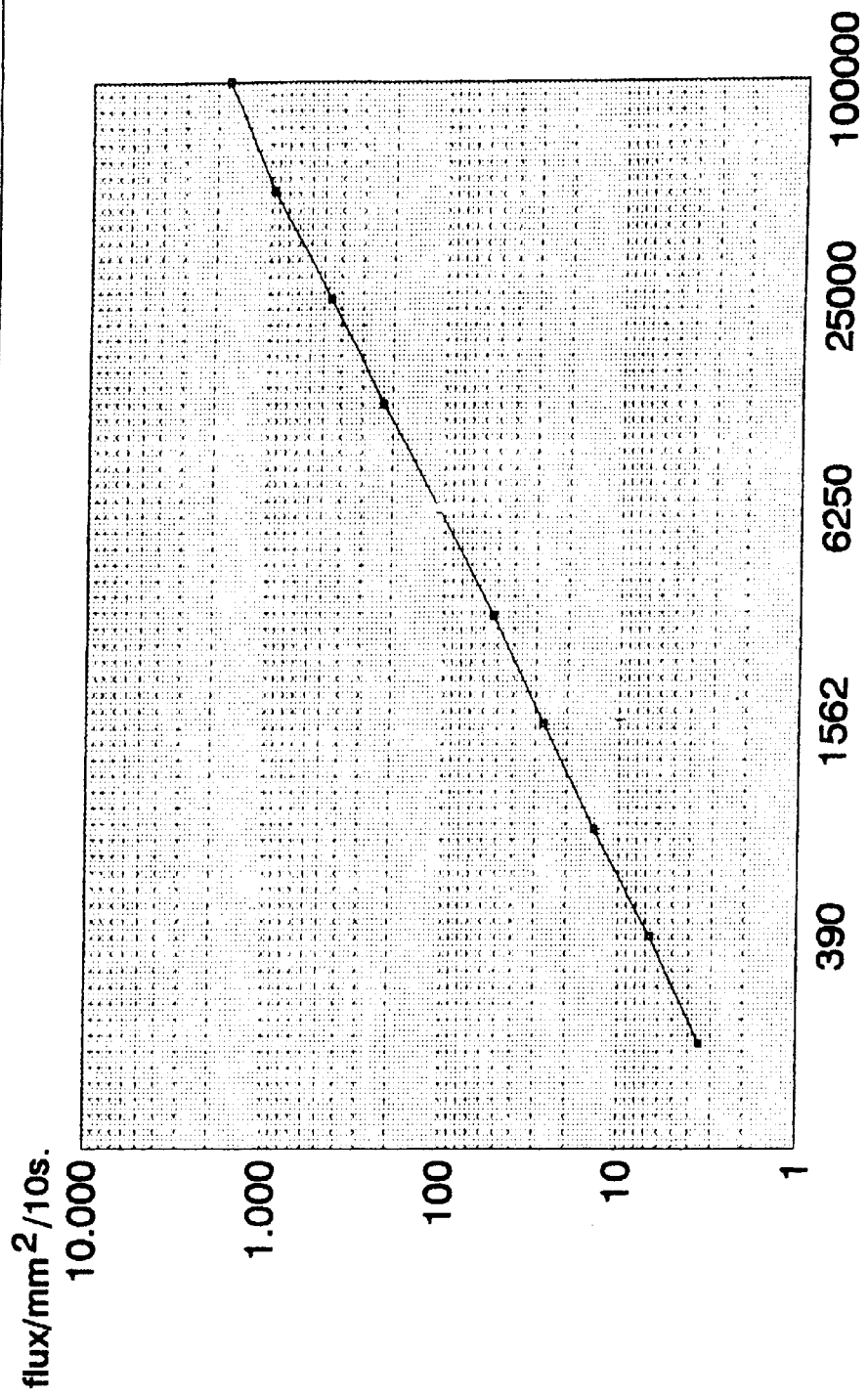

FIGS. 1 and 2 show that the chemiluminescence observed with hematin-labeled cells is proportional to the number of cells. The Figures further show that labeling of continuous cell lines as well as labeling of isolated cells is feasible.

EXAMPLE 3

Quantification of Inert Particles

As an example of inert particles, uncoated Dynabeads M-450, commercially available as a suspension of $2.10^8$ beads/ml from Dynal A.S., N-0210 Oslo, Norway, were washed and suspended at a density of 10 beads/ml in Dulbecco's PBS. After the addition of 10 μl of a hematin stock solution (1 mg/ml in DMSO), the beads were incubated at room temperature for 10 minutes while being gently mixed on a rotorack. After 10 minutes of incubation, the beads were separated from the incubation mixture by magnetic separation, washed twice with PBS, and finally resuspended at a density of $10^7$ beads/ml in PBS.

Finally, the labeled beads were plated into individual wells of a white 96 well microtiter plate so that the number of beads ranged from about 0 beads/well to about $10^6$ beads/well in a total volume of about 100 μl PBS/well.

Figure 3:
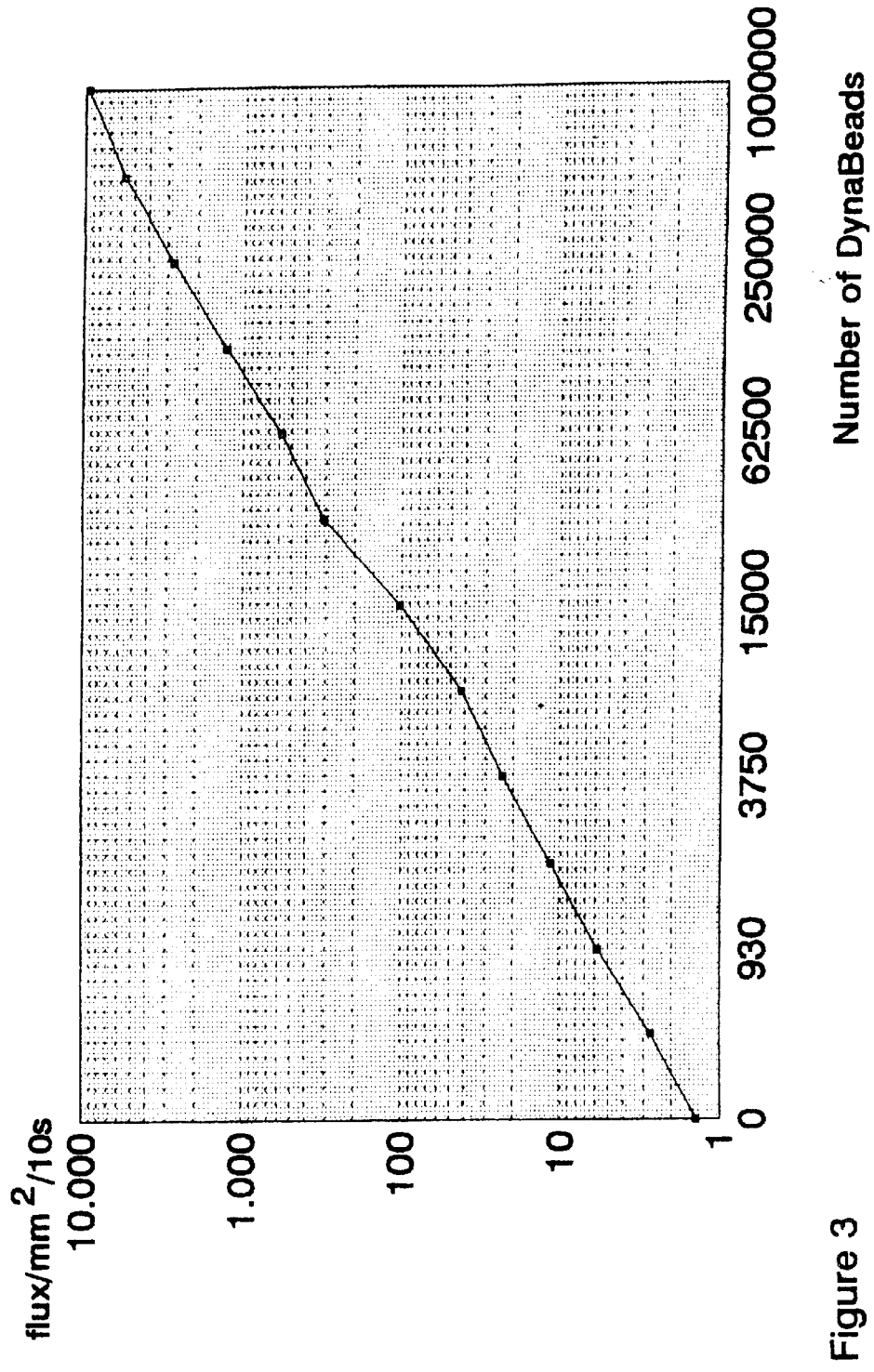
FIG. 3 shows labeling used in quantifying inert particles.

Next, the chemiluminescence (flux/mm$^2$/10 s) was detected by the addition of 100 μl stabilized luminol/oxidizer solution as previously set forth. Results of this experiment are shown in the attached FIG. 3.

EXAMPLE 4

Quantification of Microorganisms

A suspension of $10^8$ *Staphylococci aureus* was prepared in Dulbecco's PBS starting from a crude suspension of *Staphylococci aureus* grown overnight in Trypcase Soya Broth.

After washing, 1 ml of *Staphylococci aureus* suspension was labeled by the addition of 10 μl hematin stock solution (1 mg/ml in DMSO) as set forth above in the Example 3.

After 10 minutes at ambient temperature, the *Staphylococci aureus* suspension was centrifuged (450 g/5 min.) and the bacterial pellet washed with 5 ml PBS. This washing procedure was repeated twice after which the pellet of labeled bacteria was resuspended at a density of $10^8$ bacterial/ml PBS.

Next a serial dilution of bacteria was prepared in wells of a white microtiter plate from 0 up to $10^7$ bacteria in a total volume of 100 μl PBS.

Figure 4:
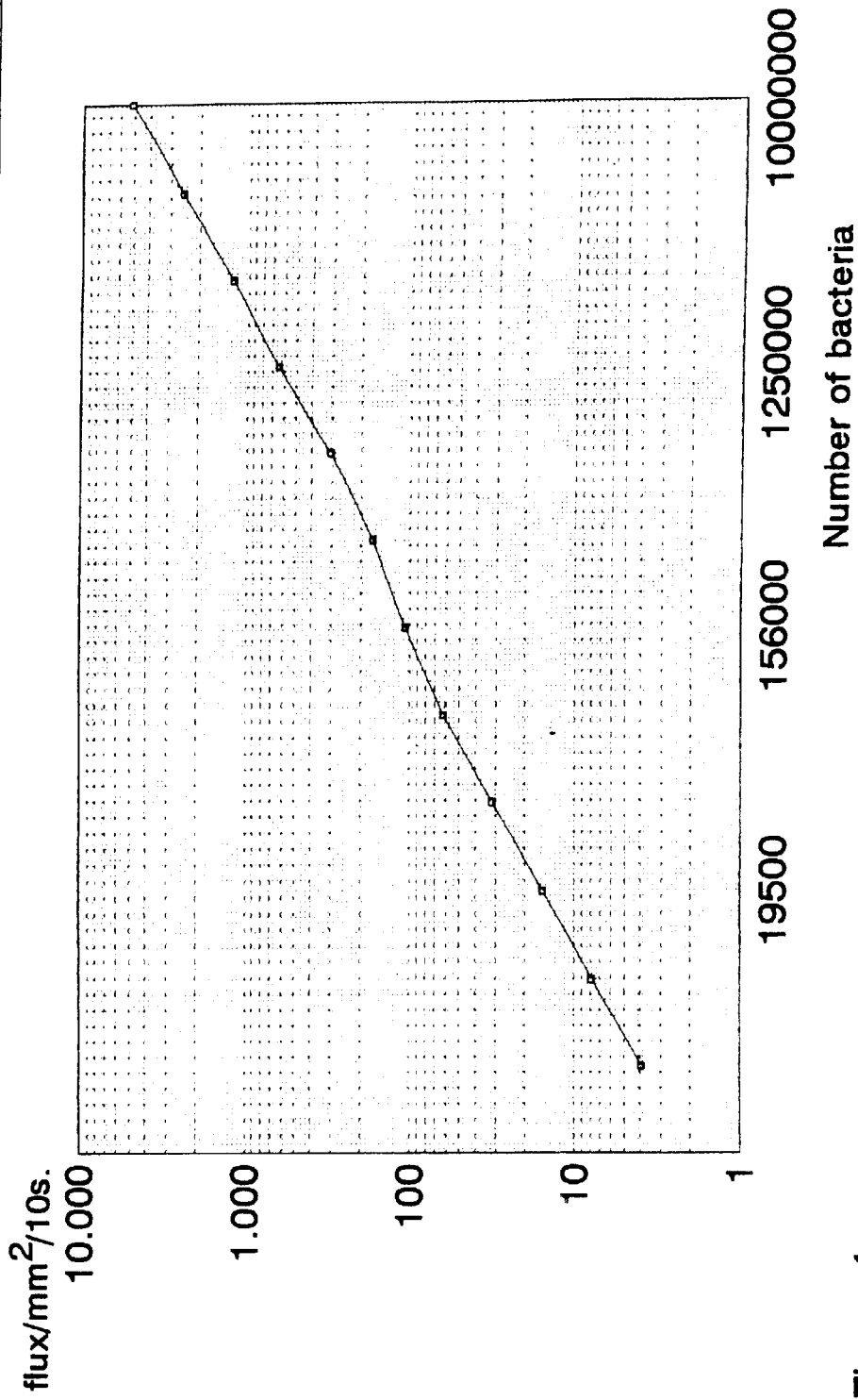
FIG. 4 shows labeling used in quantifying microorganisms.

Chemiluminescence (flux/mm$^2$/10 s) was initiated and detected as set forth above in Example 3. Results are indicated in the attached FIG. 4.

EXAMPLE 5

Quantification of the Number of Adherent Bacteria of Different Strains to Nasal Cell Monolayers Suspensions of two different strains of *Staphylococci aureus* (A, B) were prepared at a density of $10^9$/ml in PBS and labeled with hematin as set forth above in Example 4.

Figure 5:
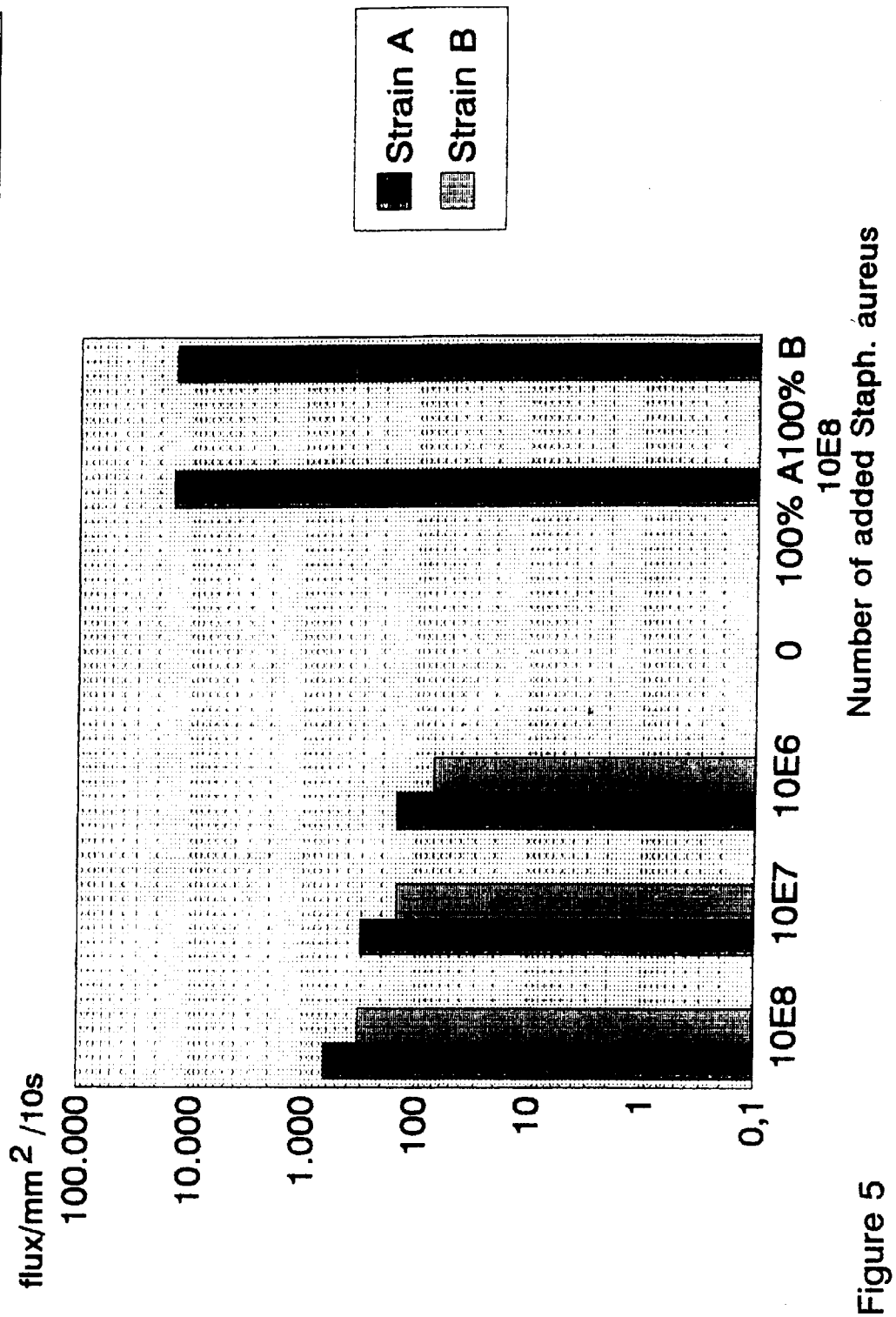
FIG. 5 shows differential adhesion of different *Staphylococci aureus* strains.

Four samples containing $10^8$, $5 \times 10^7$, $2.5 \times 10^7$, and 0 bacteria in a total volume of 100 μl were incubated with confluently grown adherent human nasal epithelial cell monolayers. After 1.5 hours of incubation at 37° C. in a humidified incubator (air, 5% $CO_2$), non-adherent bacteria were removed by gentle washing. Next, 100 μl Dulbecco's PBS were added to wells to be measured. Chemiluminescence (flux/mm$^2$/10 s) was initiated and measured as described in Example 4. Results are depicted in the attached FIG. 5 and show, differential adhesion of the different *Staphylococci aureus* strains. Also shown in FIG. 5 is the chemiluminescence of samples containing 100% of either *Staphylococci aureus* A or B.

EXAMPLE 6

Adhesion of PMA Stimulated CD4+ T-cells on Fibronectin Coated Microtiter Wells

CD4+ T-cells were isolated from a T-cell preparation according to standard procedures starting from a human whole blood sample which was first centrifuged over a Ficoli-Hypaque gradient. CD4+ T-cells were isolated by magnetic separation using Dynabeads.

Finally, CD4+ T-cells were suspended at a final concentration of $10^6$/ml in PBS. 10 μl hematin (1 mg/ml in DMSO) were added to label the T-cells as set forth above in Example 2.

After labeling and washing, CD4+ T-cells were resuspended at a density of $10^6$/ml in 50% (V/V) PBS/Hanks albumine (0.1%).

In parallel, another aliquot of CD4+ T-cells was $^{51}$Cr labeled according to standard protocols.

Next, to triplicate wells of a white microtiter plate that were either fibronectin coated (FC) or non-fibronectin coated (NFC), 50 μl PBS/HSA were added or 50 μl PBS/HSA containing $10^{-6}$ phorbol myristate acetate (PMA). For convenience, the four possible situations will be referred to as FC and NFC when PMA is not present and FC w/PMA and NFC w/PMA when PMA is present.

Next, 50 μl hematin labeled T-cells or $^{51}$Cr-labeled T-cells were added to the different well compositions. After 2 hours of incubation at 37° C. (humidified air, 5% $CO_2$), non-adherent cells were gently removed.

Next, $^{51}$Cr-labeled cells were lysed, using 100 μl of a TritonX-100 lysis solution and radioactivity determined by gamma-counting.

Figure 6:
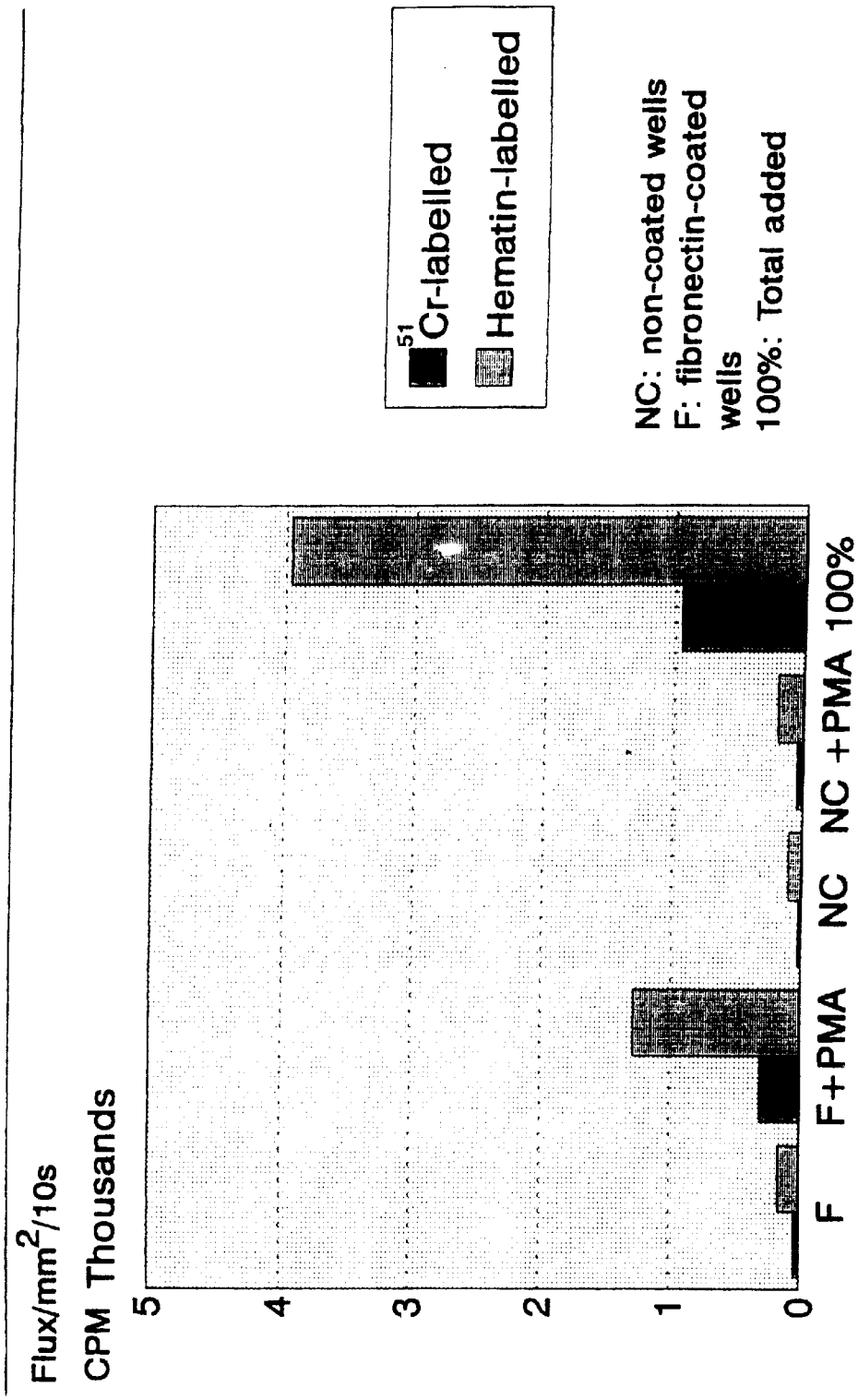
FIG. 6 shows the quantification of CD4+ T-cells.

After removing non-adherent hematin-labeled CD4+ T-cells, 100 μl PBS were added to the wells and chemiluminescence (flux/mm$^2$/10 s) was counted 10 minutes after the addition of 100 μl of the previously described stabilized luminol/oxidizer solution. Results are shown in attached FIG. 6.

EXAMPLE 7

Hematin Labeling and Virus Producing Cell Lines

DSN non-virus producing and DSNpJD214MDR1 transfected and virus producing cell monolayers were grown confluently in petri-dishes (Falcon) and labeled with 100 μg hematin contained in 10 ml Dulbecco's PBS for 10 minutes. After labeling, cells were washed 2 times with excess PBS. Controls were prepared in a similar fashion, except the PBS did not contain hematin label.

Next, 10 ml IMDM (without fetal calf serum) was added to the dishes which were then allowed to incubate overnight.

The next day, 10 μl supernatant was taken from each dish and transferred to wells of a white microtiter plate. 100 μl of the previously described stabilized luminol/oxidizer solution were added and the chemiluminescence was recorded after 10 minutes.

Figure 7:
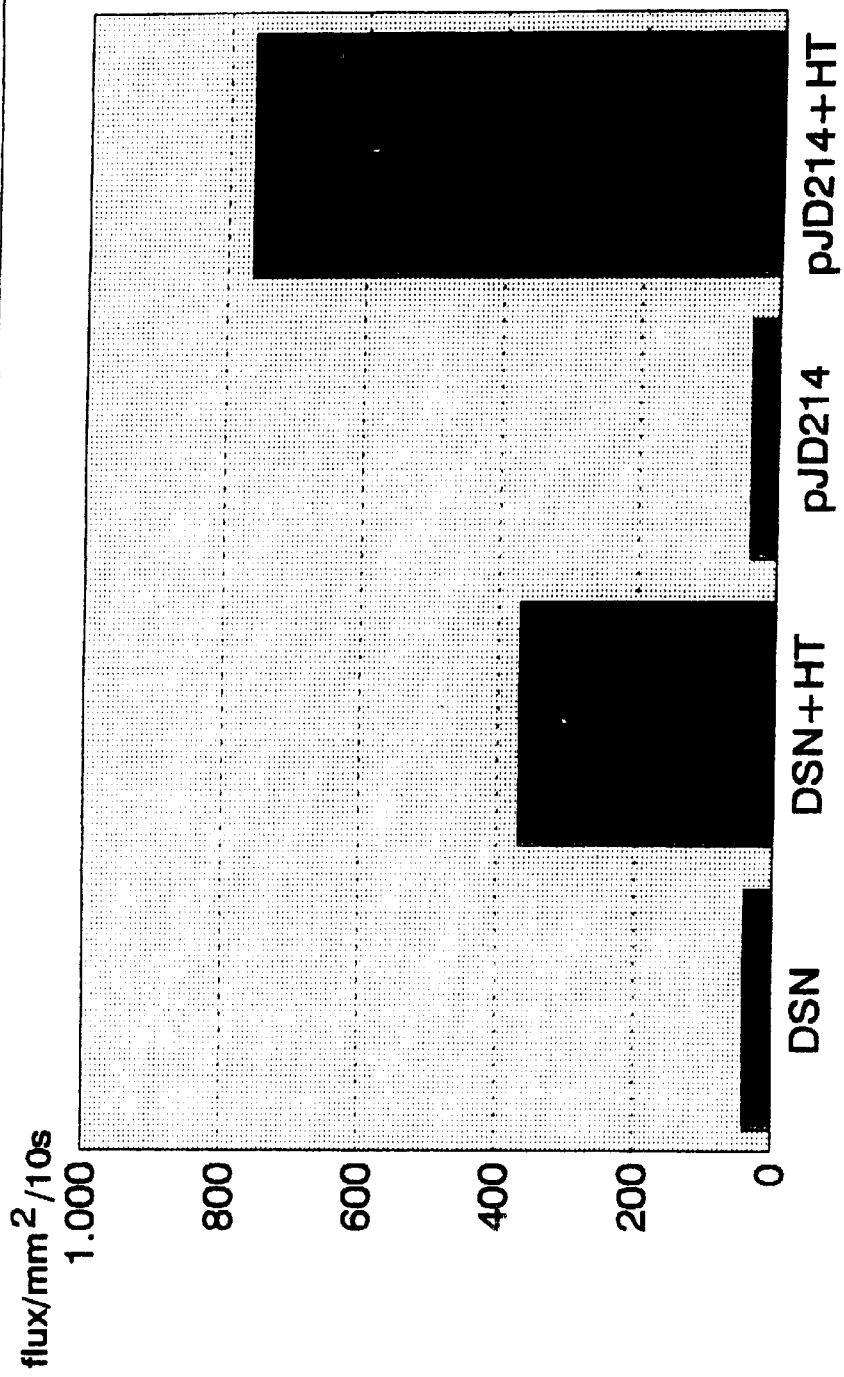
FIG. 7 shows hematin labeling of virus producing cell lines.

Results are shown in the attached FIG. 7.

No significant signal was produced with the supernatant of the controls (no label). However, a significant difference in chemiluminescence was observed with supernatant obtained from the labeled but non-virus producing line and supernatant from the labeled virus-producing monolayer.

Increase in chemiluminescence observed with supernatant derived from the latter suggests the present invention allows one to detect virus budding processes.

Finally, when monolayers of non-labeled and non-producing DSN cells were incubated with supernatant of the labeled pJD214 virus producing cell monolayer, an increase in chemiluminescence after the addition of luminol/oxidizer solution was observed with washed pjD214 cell monolayers after an initial lag phase.

Figure 8:
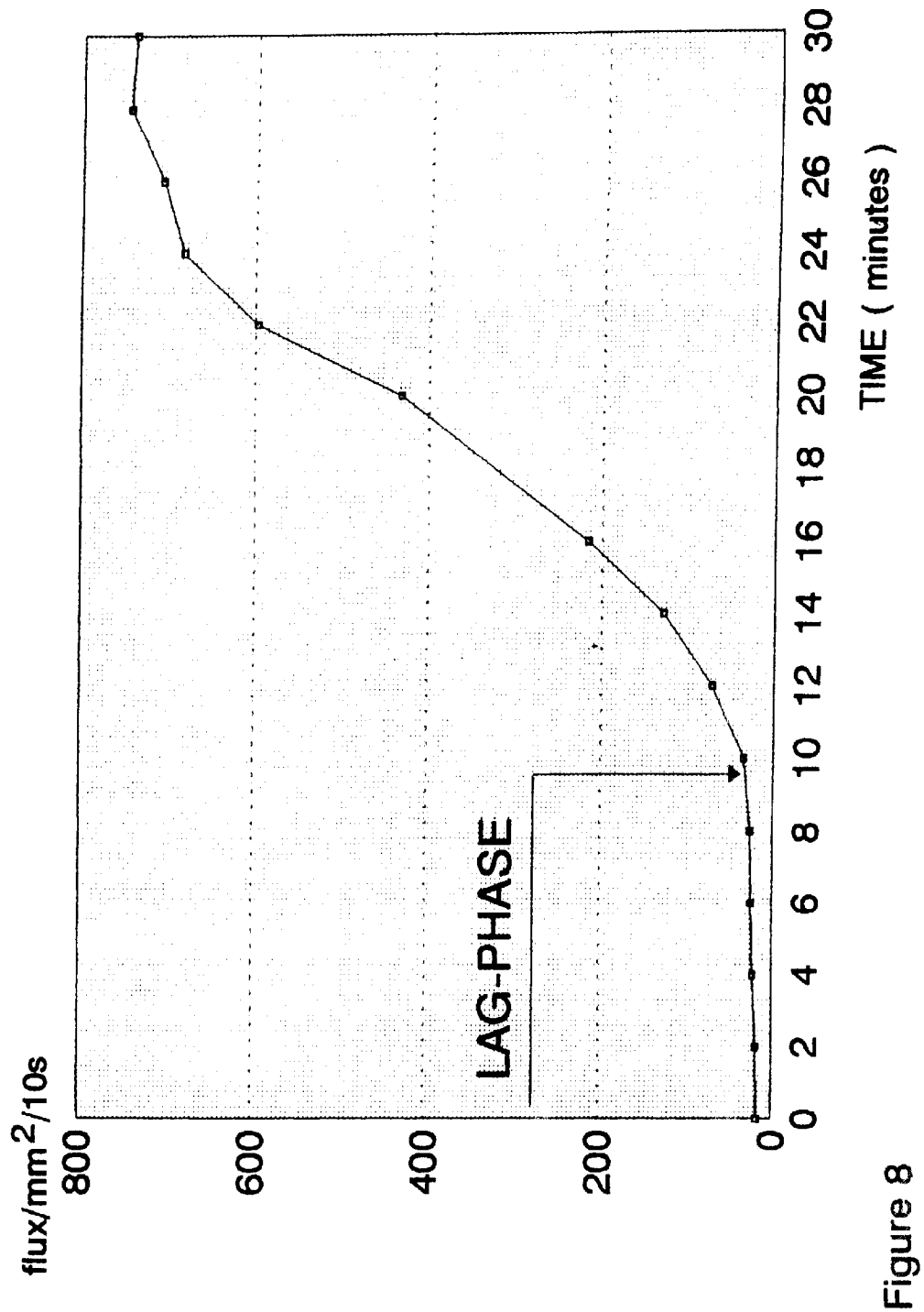
FIG. 8 shows the appearance of chemiluminescence over time in cells incubated with supernatant of labeled virus producing cells.

These results, shown in the attached FIG. 8, suggest that the stabilized luminol/oxidizer solution detects hematin-labeled virus within the DSN cells. The observed lag-phase of about 10 minutes suggests that the luminol/oxidizer solution penetrates the cells slowly before gradually becoming destabilized by the hematin brought in by the virus.

What is claimed is:

1. A process for detecting particles comprising the steps of:
    a) mixing porphyrin, in the absence of a bridging agent, with said particles for a time sufficient for the porphyrin to bind to the particles;
    b) separating the porphyrin labeled particles from the unbound porphyrin; and
    c) detecting said porphyrin labeled particles.

2. The process according to claim 1, wherein said porphyrin labeled particles are detected by chemiluminometric, radiometric, or fluorometric processes.

3. The process according to claim 1, wherein said porphyrin is a protoporphyrin IX.

4. The process according to claim 1, wherein said porphyrin is a ferroprotoporphyrin.

5. The process according to claim 4, wherein said ferriprotoporphyrin is hematin or hemin.

6. The process according to claim 1, wherein the quantification of the porphyrin labeled particles is carried out by chemiluminometric processes and wherein a luminescent probe and an oxidizer are admixed with the separated porphyrin labeled particles.

7. The process according to claim 6, wherein said luminescent probe is a 2,3-dihydro-1,4-phthalazinedione.

8. The process according to claim 6, wherein said oxidizer is selected from the group consisting of perborate, hydrogen peroxide, hydroperoxide, endoperoxide, and an oxidizer producing enzyme.

9. The process according to claim 6, wherein the chemiluminometric process is additionally conducted in the presence of a chelator and a buffer to maintain pH.

10. The process according to claim 9, wherein the chelator is EDTA or desferrioxamine.

11. The process according to claim 9, wherein the buffer is a borate, carbonate, tris(hydroxymethyl) aminomethane, or phosphate buffer.

12. The process according to claim 1, wherein said porphyrin is an isotopically labeled porphyrin and detection of the porphyrin labeled particles is carried out by radiometric processes.

13. The process according to claim 12, wherein said porphyrin is isotopically labeled with an atom selected from the group consisting of carbon-14, chlorine-36, cobalt-(57, 58, 60), gadolinium-153, iron-(55, 59), nickel-63, tritium, iodine-125, tin-113, zinc-65, phosphorus-(32, 33).

14. The process according to claim 1, wherein detection is conducted by radiometric processes in which SPA beads are combined with porphyrin labeled with iodine-125.

15. The process according to claim 1, wherein said porphyrin labeled particles are detected by virtue of the fluorescence of the porphyrin label.

16. The process according to claim 1, wherein the amount of porphyrin used for labeling is from about $10^3$ M to about $10^5$ M.

17. The process according to claim 1 wherein the particle to be detected is a molecule, bead, microorganism or cell.

18. An adhesion assay comprising the steps of:
    a) providing a suspension of particles to be tested;
    b) mixing porphyrin, in the absence of a bridging agent, with said suspension;
    c) separating porphyrin labeled particles from unbound porphyrin;
    d) incubating the porphyrin labeled particles with a target surface;
    e) removing non-adherent porphyrin labeled particles; and
    f) detecting the adherent porphyrin labeled particles.

19. The adhesion assay of claim 18, wherein the porphyrin labeled particles are separated from unbound porphyrin by centrifugation, magnetic separation, or filtration.

20. The adhesion assay of claim 18, wherein the adherent porphyrin labeled particles are detected by radiometric, fluorometric, or chemiluminometric processes.

21. A particle diameter or surface size assay comprising the steps of:
    a) providing a suspension of a predetermined number of particles to be tested;
    b) mixing porphyrin, in the absence of a bridging agent, with the suspension;
    c) removing porphyrin labeled particles from unbound porphyrin;
    d) detecting a signal generated by the predetermined number of particles; and
    e) calculating the signal per particle as an indication of the diameter or surface size of the particles.

22. The particle diameter or surface size assay of claim 21, wherein the porphyrin labeled particles are removed from unbound porphyrin by centrifugation, magnetic separation, or filtration.

23. The particle diameter or surface size assay of claim 21, wherein the signal generated by the predetermined number of particles is detected by radiometric, fluorometric, or chemiluminometric processes.

24. A particle uptake study comprising the steps of:
    a) providing a suspension of particles to be studied;
    b) mixing porphyrin, in the absence of a bridging agent, with the suspension;
    c) removing unbound porphyrin from porphyrin labeled particles;
    d) resuspending labeled particles in an appropriate medium;

e) injecting the labeled particles and appropriate medium into biologic objects; and f) tracing the injected particles.

25. The particle uptake study of claim 24, wherein the unbound porphyrin is removed from the porphyrin labeled particles by centrifugation, magnetic separation, or filtration.

26. The particle uptake study of claim 24, wherein the injected particles are traced by radiometric, fluorometric, or chemiluminometric processes.

27. An assay kit for detecting particles, in the absence of a bridging agent, comprising a first container containing porphyrin and a set of directions for chemiluminometric, radiometric, or fluorometric processes.

28. The assay kit according to claim 27, wherein the porphyrin is present in sufficient quantity to conduct multiple detection assays.

29. The assay kit according to claim 27, further comprising a second container containing a stabilized mixture of luminescence precursor and oxidizer.

30. The assay kit according to claim 29, wherein the second container further contains a buffer substance and a chelator.

31. The assay kit according to claim 27, wherein the porphyrin is isotopically labeled with a beta emitter and wherein the assay kit further comprises a second container containing a scintillation cocktail.

32. A composition comprising a porphyrin bound particle, wherein there is no bridging agent to couple the porphyrin to the particle.

33. The composition of claim 32, wherein the particle is a drug, drug metabolite, hormone, peptide, nucleotide, neurotransmitter, cholesterol, growth factor, oligonucleotide, antibody, antigen-binding fragment, serum protein, enzyme, polynucleotide, intracellular organelle, cell surface antigen, avidin, biotin, binding protein, nucleic acid, membrane probe, or nucleic acid probe.

* * * * *